United States Patent [19]

Baptist et al.

[11] Patent Number: 4,472,634
[45] Date of Patent: Sep. 18, 1984

[54] APPARATUS FOR DETERMINING THE DENSITY OF UNOCCUPIED ELECTRONIC STATES OF A MATERIAL

[75] Inventors: Robert Baptist; Gérard Chauvet, both of Grenoble, France

[73] Assignee: Commissariat A L'Energie Atomique, Paris, France

[21] Appl. No.: 373,240

[22] Filed: Apr. 29, 1982

[30] Foreign Application Priority Data

May 14, 1981 [FR] France ................................ 81 09613

[51] Int. Cl.$^3$ .............................................. G01J 1/42
[52] U.S. Cl. .................................... 250/372; 250/399; 250/459.1
[58] Field of Search ............ 250/372, 306, 399, 458.1, 250/459.1; 356/305, 311, 317, 318, 328, 329

[56] References Cited

U.S. PATENT DOCUMENTS 4,253,765  3/1981  Kato et al. ........................... 356/328

FOREIGN PATENT DOCUMENTS 2428836  1/1980  France .

OTHER PUBLICATIONS

Kittel, *Introduction to Solid State Physics*, 6th edition, Wiley & Sons, New York, 1976, pp. 348–350.

Applied Physics, Vol. 18, 1979, Denninger et al., "A VUV Isochromat Spectrometer for Surface Analysis".
Physical Review B, solid state third series, Vol. 7, No. 8, 1973, Turtle et al., Densities of Unfilled One-Electron Levels in Elements Vanadium & Iron through Zinc by Means of X-ray Continuum Isochromats".

*Primary Examiner*—Janice A. Howell
*Attorney, Agent, or Firm*—Pearne, Gordon, Sessions, McCoy, Granger & Tilberry

[57] ABSTRACT

The invention relates to an apparatus for determining the electron states of a material. This apparatus comprises an enclosure containing a material, means for producing electrons of energy $E_i$ such, that on then penetrating the material, they acquire an energy $E_f$ below $E_i$, accompanied by an emission of photons having different wavelengths. The apparatus also comprises another enclosure equipped with a tube entering the vacuum enclosure and provided with an entrance slit and another tube provided with a regulatable exit slit. The apparatus also comprises a grating located in the other enclosure and etched with lines, whilst being able to rotate about an axis parallel to these lines in order to select photons of the same wavelength. The apparatus finally has means for detecting the selected photons.

Application to the determination of the forbidden band of a semiconductor.

6 Claims, 5 Drawing Figures

APPARATUS FOR DETERMINING THE DENSITY OF UNOCCUPIED ELECTRONIC STATES OF A MATERIAL

BACKGROUND OF THE INVENTION

The present invention relates to an apparatus for determining the density of unoccupied electron states of a material located above the Fermi level, as well as for analyzing by ultraviolet fluorescence of a material excited by electrons. This apparatus associated with a photoemission apparatus, makes it possible to determine the electron structure of a material, the value of the forbidden energy band for new semiconductor or insulants, as well as the orbital character of electrons belonging to the conduction band of this material.

In a metal, the Fermi level coincides with the highest energy level effectively occupied by electrons. Thus, in the case of a metallic material, the Fermi level is located in the conduction band, whereas in insulants and semiconductors the Fermi level is located between the conduction band and the valence band, i.e. in the forbidden energy band.

In order to determine the density of the unoccupied electron states located above the Fermi level of a material, a sample of the material is bombarded by means of an electron beam having an adequate intensity and of initial energy $E_i$. On penetrating the sample, the electrons are decelerated and have a certain probability of passing from their initial energy $E_i$ to final energy states $E_f$ below $E_i$. Generally, the passage between these two energy levels is accompanied by the emission of photons, whose energy $h\nu_{if}$ is such that $h\nu_{if} = E_i - E_f$.

As a first approximation, the number of photons emitted having the energy $h\nu_{if}$ is proportional to the density of the unoccupied electron states $n(E_f)$ dependent on the energy level $E_f$. A scan in initial energy $E_i$ of the incident electrons makes it possible by collecting, using appropriate systems, a fixed energy photon to determine the density of the electron states $n(g)$.

The study of fixed energy photons, i.e. having the same wavelength, coming from a sample bombarded with an electron beam is known as "Bremstrahlung Isochromat Spectroscopy" or by the abbreviation "BIS", i.e. braking radiation isochromatic spectroscopy. It can also be called "inverse photoemission".

The hitherto known apparatus make it possible to detect either high energy photons, i.e. the energy of the photons is above 0.5 keV, or low energy photons, i.e. the energy of the photons is below 10 eV.

One apparatus which detects high energy photons is described in the article entitled "Densities of Unfilled One-Electron Levels in the Elements Vanadium and Iron through Zinc by Means of X-Ray Continuum Isochromats", which appeared in the Journal Physical Review B, 3rd series, Vol. 7, No. 8, pp. 3411 to 3419. This article describes an apparatus enabling the detection of photons which have an energy equal to 0.53 keV of an X-radiation by means of a fixed X-monochromator. The use of an X-monochromator, which is difficult to regulate, and the fact that the apparatus has a large size make is far from easy to use.

An apparatus detecting low energy photons is described in an article entitled "A VUV Isochromat Spectrometer for Surface Analysis", published in Applied Physics, 18, 1979, pp. 375 to 380. This article describes an apparatus enabling the detection only of photons with an energy equal to 9.7 eV of ultraviolet radiation by means of a Geiger-Muller counter placed behind a lithium fluoride window.

The main disadvantage of these two apparatus, as well as all other known apparatus, is that it is only possible to detect photons with a clearly defined energy level, i.e. they only operate at a single wavelength.

BRIEF SUMMARY OF THE INVENTION

The present invention relates to an apparatus which obviates these disadvantages and in particular makes it possible to work in a wide wavelength range. The apparatus according to the invention in particular makes it possible to detect and analyse photons, whose energy is between 10 and 100 eV, i.e. whose wavelength is between 100 and 1000 Å.

More specifically, the present invention relates to an apparatus for determining the density of the unoccupied electron states of a material located above the Fermi level and for carrying out the analysis by ultraviolet fluorescence of a material excited by electrons comprising a vacuum enclosure which can contain a sample of a material; means for creating an electron beam of energy $E_i$ having an adequate intensity to ensure that their interaction with the sample can easily be detected, the electrons then acquiring energy levels $E_f$ below $E_i$, the passage between the two energy levels accompanying an emission of photons, whose energy $h\nu_{if}$ is such that $h\nu_{if} = E_i - E_f$; means for performing a scan in energy $E_i$; and means for measuring the radiation coming from the sample; wherein the measuring means are placed under a vacuum and comprise a second enclosure provided with two tubes, which are inclined relative to one another, a first tube entering the vacuum enclosure, provided with a regulatable width entrance slit located in the vacuum enclosure, and a second tube provided with a regulatable exit slit; a diffraction grating able to rotate about an axis parallel to the etching marks thereof, enabling the selection of one of the wavelengths of the emitted photons, said grating being located in the second enclosure; means for rotating the said grating, its rotation angle being linked with the selection of the wavelength; and means for detecting photons of the same wavelength selected by the grating, said means facing the exit slit.

According to a preferred embodiment of the invention, the grating permits the selection of wavelengths between 100 and 1000 Å.

According to a preferred embodiment of the invention, the means for producing the electron beam comprise a filament, located in the vacuum enclosure and raised to a potential V compared with the sample.

The filament heating is preferably controlled in a pulsed manner, as is the detection and counting of the photons having the same wavelength, the heating control alternating with that of the detection and the counting.

According to another preferred embodiment of the invention, the first tube incorporates a metal bellows permitting the adjustment of the position of the measuring means compared with that of the sample, when the apparatus is operating.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
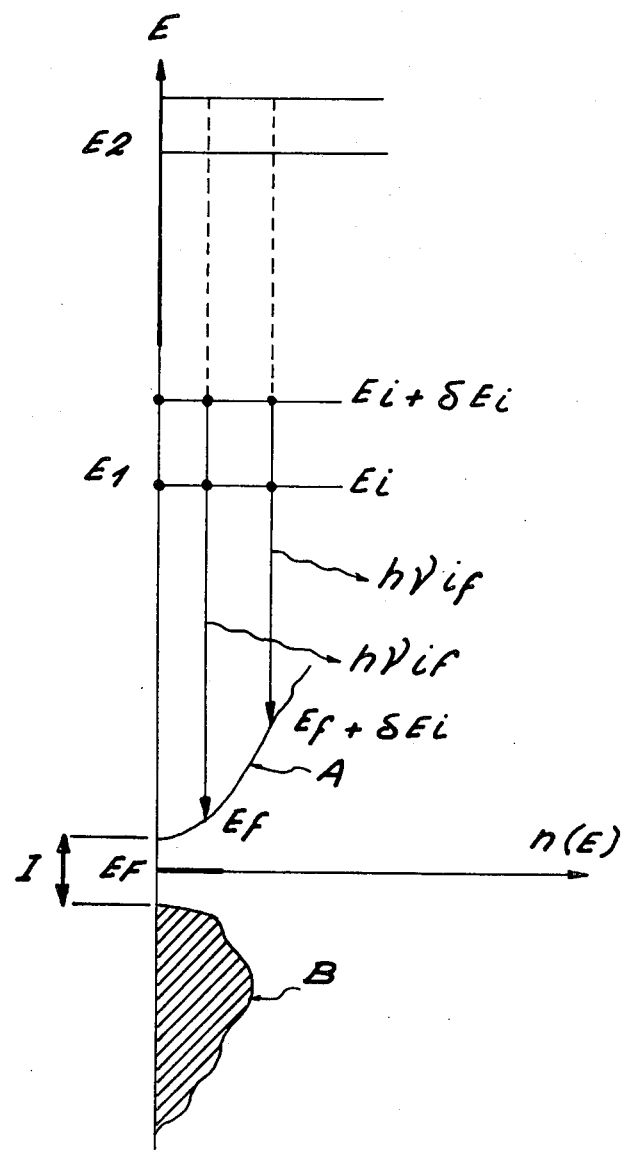
FIG. 1 the physical principle of the invention.

In FIG. 1, the density of the occupied electron states separated from a density of unoccupied electron states, the state density being designated n(E), by a forbidden band (I) is plotted on the abscissa, whilst the energies E is plotted on the ordinate.

It is pointed out that an electron of initial energy $E_i$ effects a transition to a final energy state $E_f$, whilst emitting a photon of energy $h\nu_{if}$. In the same way, it can be seen that an electron of energy $E_i + \Delta E_i$ effects a transition to a final energy state $E_f + \Delta E_i$, whilst again emitting a photon of the same energy $h\nu_{if}$. The measurement of the number of photons of energy $h\nu_{if}$ emitted when energy $E_i$ varies makes it possible to plot curve A representing the density of the unoccupied electron states and also the position of the bottom of the forbidden band compared with the Fermi level designated $E_f$.

This is complementary to the photoemission, which makes is possible to determine the form (curve B) of the density of the occupied electron states, as well as the position of the top of the forbidden band compared with the Fermi level. Thus, the configuration of the two curves A and B enables the determination of the forbidden band value.

Figure 2:
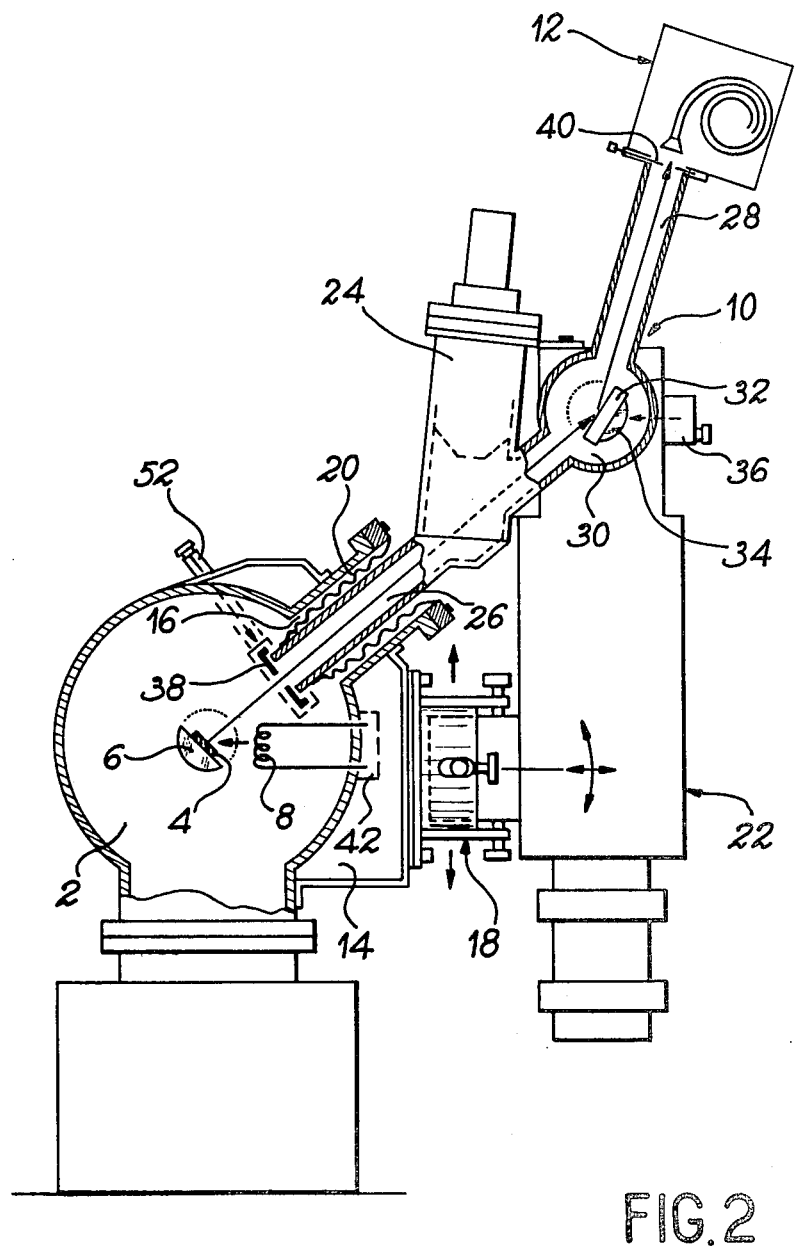
FIG. 2 diagrammatically, the apparatus according to the invention.

FIG. 2 shows an apparatus according to the invention, which comprises inter alia a vacuum enclosure 2 in which are placed a sample of a material 4 to be investigated and which is positioned on a support 6, as well as a heated filament 8 enabling the production of an electron beam having an intensity at least equal to 1 mA and of initial energy $E_i$, said electrons being able to penetrate sample 4. On penetrating the sample, these electrons are decelerated and can acquire final energy levels $E_f$ below $E_i$. The conservation of the energy between the initial energy and the final energy leads to the emission of photons of energy $h\nu_{if}$.

The value of said energy $h\nu_{if}$, i.e. of wavelength $\lambda_{if}$ ($\lambda_{if} = c/\nu_{if}$ being the speed of light) is dependent on the initial energy and the final energy of the electrons. The initial energy $E_i$ can be modified by performing an energy scan. The number of electrons acquiring the final energy $E_f$ depends, in a first approximation, on the density of the unoccupied electron states $n(E_f)$ of the material above the Fermi level, i.e. the number of emitted photons depends on the value of $E_i$ and on the density of the electron states $n(E_f)$.

Therefore, for determining the number $n(E_f)$, it is necessary to carry out a first scan of energy $E_i$ about an energy level $E_1$, whilst counting the number of photons having e.g. wavelength $\lambda_1$. This can be followed by a scan in energy $E_i$ about an energy level $E_2$, whilst detecting and measuring the number of photons of wavelength $\lambda_2$, etc. This makes it possible to define the orbital character of the final energy states reached (cf FIG. 1).

The photons of the same wavelength are selected by means of a general reference monochromator 10, after which they are detected and counted by means of a detector 12 of the channeltron type, this being a tubular photomultiplier used as a pulse counter.

This monochromator 10 is mounted on a chassis 14 enabling it to be fixed to the vacuum enclosure 2 level with an opening 16 made in the said enclosure. A regulating or setting system 18 and a metal bellows 20 are provided on chassis 14 for ensuring the correct positioning of the monochromator on enclosure 2 in such a way that the diffraction grating 32, constituting the monochromator, receives the photons from sample 4 and after dispersion by the grating the photons of the same energy, selected by the monochromator, arrive correctly on detector 12.

In order to produce a high vacuum of approximately $10^{-9}$ millibars (mb) in monochromator 10, which makes it possible to retain a vacuum of $10^{-11}$ mb in enclosure 2, the monochromator is connected to a pumping system 22 having e.g. in per se known manner a liquid nitrogen trap, a turbomolecular pump, a primary pump and various valves.

In addition, the apparatus shown in FIG. 2 can be equipped with a valve 24 which, if necessary, permits the isolation of monochromator 10, so as to be able to preserve the vacuum produced in enclosure 2. This can be used e.g. for changing the grating.

More specifically, the monochromator 10 can comprise two tubes 26, 28 forming between them a fixed angle of 142° and interconnected by means of an enclosure 30 containing diffraction grating 32 supported by support 34. This grating can rotate about an axis perpendicular to the plane of the drawing, i.e. the axis is parallel to the etched lines of the grating. Grating 32, which has an angular displacement of approximately 8°, is a grating working in a vacuum ultraviolet. It makes it possible to select photons, whose wavelength is between 100 and 1000 Å. The wavelength is selected by modifying the position of the grating e.g. by means of a sine arm coupled to a per se known stepping motor 36 connected by a ultra-high vacuum passage to support 34.

The end of tube 26 entering vacuum enclosure 2 is provided with a slit 38 having a regulatable aperture and constituting the entrance slit of monochromator 10 through which pass the photons emitted by sample 4. This slit is located within the vacuum enclosure 2 and the end of tube 28 facing detector 12 is provided with a regulatable slit 40 constituting the exit of the monochromator through which pass the photons with the selected wavelength in order to be counted by detector 12.

Figure 3:
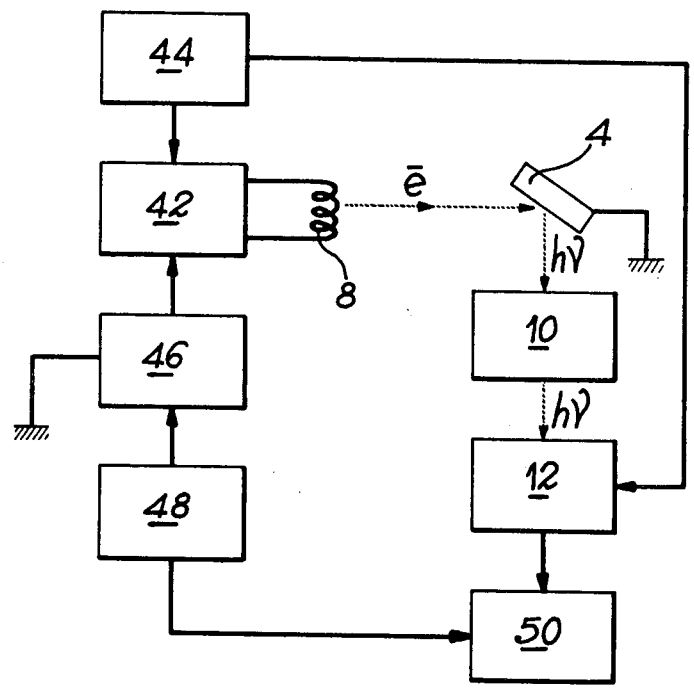
FIG. 3 a block diagram of the apparatus of FIG. 2.

FIG. 3 shows a block diagram of the apparatus according to the invention enabling the explanation of the operating principles thereof.

Filament 8 constituting the electron source is heated in a pulsed manner by means of a heating device 42 controlled by a pulsing circuit 44, whose function is to block and unblock detector 12. Moreover, filament 8 is raised to a certain potential V compared with sample 4 by means of a device 46 used for applying the initial energy $E_i$ to the electrons bombarding the sample 4.

After the heating time of filament 8 (2 ms), the heating is cut off by means of control circuit 44 in such a way that the filament is equipotential. The interruption of the heating unblocks the count (for 8 ms) by means of detector 12 of the photons of the same energy selected by monochromator 10.

Device 46 is connected to a control circuit 48 enabling the performance of a voltage scan and consequently modify the energy $E_i$ of the electrons on detecting photons of the same energy. The control circuit 48 and detector 12 are connected to a multichannel selector 50, which makes it possible to obtain the Bremstrahlung Isochromat Spectrum or BIS for the detection of photons of the same energy.

Figure 4:
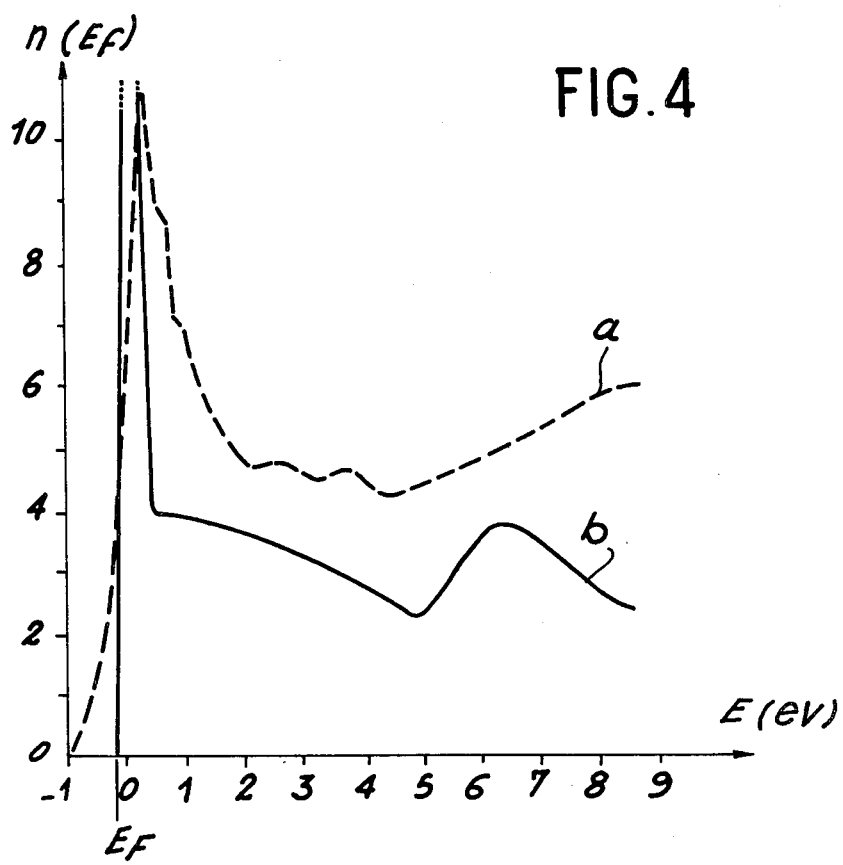
FIG. 4 the Bremstrahlung isochromat spectrum of platinum for photons having an energy of 24.8 electron volts, i.e. a wavelength of 500 angströms, the curves giving the number of unoccupied electron states $n(E_f)$ or the number of photons of 500 Å as a function of the initial energy of the electrons $E_i$, expressed in eV.

An example of a BIS is shown in FIG. 4 and gives in a first approximation the number of unoccupied electrons states $n(E_f)$ as a function of the energy $E_i$ of the electrons expressed in eV. This is in fact the spectrum of platinum for photons having an energy of 24.8 eV or a wavelength of 500 Å, curve A representing the experimental curve and curve B the theoretical curve.

The curve of FIG. 4 corresponds to a scan of $E_i$ around value $E_i=24.8$ eV. The time necessary for its acquisition is approximately 1 hour. If it is desired to record a new spectrum with a second value $E_i$ about $E_2=50$ eV a further hour is required.

The acquisition time for the same amount of information can be reduced by detecting the photons by means of a multidetector (wafer of microchannels associated with a resitive anode of localization xy). In this case, the exit slit 40 of monochromator 10 can be eliminated or have a large aperture in order to simultaneously detect the photons in a wide range of wavelengths. This improvement to the acquisition time makes it possible to envisage the use of a low energy electron gun, whose beam current is too low in the present state of the art. Thus, by means of a variation of the incidence angle on the sample, it is possible to measure the dispersion curves $E(\vec{k})$ ($\vec{k}$ being the wave vector) of the unoccupied states. This measurement would be the counterpart of the determination of the dispersion curve $E(\vec{k})$ of the occupied states obtained in angular photoemission in the range 10 to 100 eV.

In order to improve the resolution of the apparatus according to the invention, the size of the entrance slit 38 can be modified as a function of the incident energy $E_i$ of the electrons by means of a control device 52. Thus, for low energy levels of the incident electrons (below 20 eV) the electron emission current is low and the monochromator slits have to be opened, which only slightly modifies the energy resolution in this range, but increases the counting rate. Conversely, for high energy levels, the emission current increases considerably and therefore so does the counting rate and it is possible to work with narrower slits, which increases the resolution.

For example, for an ultraviolet grating with 550 lines per millimeter, corresponding to a dispersion of 20 Å/mm and on fixing an energy resolution of the detected photons of 1 eV, the entrance slit 38 is 0.1 for an energy of 50 eV and 0.6 mm for an energy of 20 eV.

To increase the resolution of the apparatus, it is possible to use an ultraviolet grating having two times as many lines per millimeter, whilst retaining the same aberration corrections, which doubles the dispersion and therefore the resolution for the same slits.

Compared with the prior art apparatus, this apparatus is very easy to use. Thus, the monochromator only measures 60 cm, which is certainly not bulky. It can also be easily positioned relative to the sample by means of bellows 20, which is fixed to the tube 26 of monochromator 10. In addition, no problems are encountered in the optical setting of the grating.

Moreover, the fact that the invention makes it possible to choose different energy values for the photons, i.e. different wavelengths, whilst obtaining the BIS for each of these energy levels by carrying out a scan of energy $E_i$ enables the determination of the effective cross-sections of the BIS phenomenon as a function of the energy of the incident electrons, which is not possible with the prior art apparatus.

Moreover, the apparatus according to the invention makes it possible to establish for a given material the ultraviolet fluorescent spectrum of the electronexcited material. The spectrum is established by bombarding the sample with an electron beam of fixed energy and by detecting the photons emitted by carrying out a wavelength scan thereof. This is possible as a result of the movable grating, whose rotation can be controlled by a stepping motor.

In this case, the electron bombardment is used for exciting an electron linked with the material on passing it from an energy state $E_a$ to an energy state $E_b$, which is above the Fermi level $E_F$. The deexcitation of the thus created vacancy on level $E_a$ by electrons, whose energy $E_i$ is between $E_a$ and $E_F$ leads to the emission of a photon of energy hv such that $h\nu = E_i - E_a$.

Figure 5:
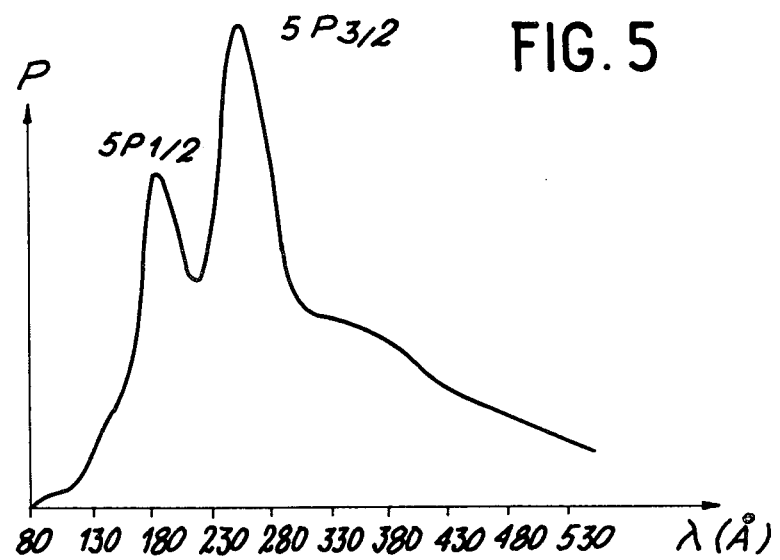
FIG. 5 the number of photons P emitted by ultraviolet fluorescence of a platinum sample as a function of the wavelength $\lambda$ expressed in Å.

The UV fluorescent spectrum is characteristic of the sample, which makes it possible to check its composition. An example in the case of platinum is shown in FIG. 5. In FIG. 5 the wavelength λ expressed in Å plotted on the abscissa and the number of photons P emitted by fluorescence by a platinum sample excited by electrons of fixed energy and equal to 500 eV is plotted on the ordinate. The observed doublet $5P_{\frac{1}{2}}$ and $5P_{3/2}$ corresponds to the deexcitation of the vacancies created in the atomic sublayers $5P_{\frac{1}{2}}$ and $5P_{3/2}$.

By studying the BIS, it is possible to investigate absorption, corrosion and oxidation phenomena of a material. In addition, in a semiconductor, the fraction of the forbidden band between $E_F$ and the first unoccupied states can be directly determined on the spectra.

What is claimed is:

1. An apparatus for determining the density of the unoccupied electron states of a material located above the Fermi level and for carrying out the analysis by ultraviolet fluorescence of a material excited by electrons comprising a vacuum enclosure which can contain a sample of a material; means for creating an electron beam of energy $E_i$ for interacting with the sample, said beam having an adequate intensity to ensure that the interaction of said beam with the sample can easily be detected, the electrons then acquiring energy levels $E_f$ below $E_i$, the passage between the two energy levels accompanying an emission of photons, whose energy $h\nu_{if}$ is such that $h\nu_{if} = E_i - E_f$; means for performing a scan in energy $E_i$; and means for measuring the radiation coming from the sample; wherein the measuring means are placed under a vacuum and comprise a second enclosure provided with two tubes, which are inclined relative to one another, a first tube entering the vacuum enclosure, provided with a regulatable width entrance slit located in the vacuum enclosure, and a second tube provided with a regulatable exit slit; a diffraction grating having etching marks, said grating able to rotate about an axis parallel to said etching marks, thus enabling the selection of one of the wavelengths of the emitted photons, said grating being located in the second enclosure; means for rotating the said grating, its rotation angle being linked with the selection of the wavelength; and means for detecting photons of the same wavelength selected by the grating, said means facing the exit slit.

2. An apparatus according to claim 1, wherein the grating makes it possible to select wavelengths between 100 and 1000 Å.

3. An apparatus according to claims 1 or 2, wherein the intensity of the electron beam is at least approximately 1 mA.

4. An apparatus according to claim 1, wherein the detection means comprise a tubular photomultiplier.

5. An apparatus according to claim 1, wherein the means for producing the electron beam comprise a filament located in a vacuum enclosure and raised to a potential V compared with the sample, whilst also comprising means for controlling in a pulsed, alternating manner the heating of the filament and the detection and counting of photons of the same wavelength.

6. An apparatus according to claim 1, wherein the first tube also comprises a metal bellows enabling the adjustment of the position of the measuring means with respect to the sample, when the apparatus is operating.

* * * * *